United States Patent

Geprägs et al.

Patent Number: 6,077,965
Date of Patent: Jun. 20, 2000

[54] METAL COMPLEXES WITH AN ADAMANTANE-LIKE STRUCTURE

[75] Inventors: Michael Geprägs, Bobenheim-Roxheim; Rainer Stürmer, Rödersheim; Horst Weiss, Karlsruhe; Susanne Steiger, Römerberg, all of Germany

[73] Assignee: BASF Aktiengesellschaft, Germany

[21] Appl. No.: 09/284,412

[22] PCT Filed: Sep. 23, 1997

[86] PCT No.: PCT/EP97/05206

§ 371 Date: Apr. 14, 1999

§ 102(e) Date: Apr. 14, 1999

[87] PCT Pub. No.: WO98/16534

PCT Pub. Date: Apr. 23, 1998

[30] Foreign Application Priority Data

Oct. 14, 1996 [DE] Germany ............. 196 42 354

[51] Int. Cl.$^7$ ................. C07F 7/00; C07F 9/00; C07F 11/00
[52] U.S. Cl. ................. 556/42; 556/43; 556/52; 556/54; 556/56; 556/57; 556/58; 502/103; 502/117; 526/160
[58] Field of Search ................. 556/42, 43, 52, 556/54, 56, 57, 58; 502/103, 117; 526/160

[56] References Cited

U.S. PATENT DOCUMENTS 5,707,913  1/1998  Schlund et al. ............. 502/102

FOREIGN PATENT DOCUMENTS 44 20 783  12/1995  Germany .
05/06071   3/1995   WIPO .

OTHER PUBLICATIONS

Chem. Abst, Inorg. Chem. Acta, Bd. 212, N4. 1–2, S. 281–288 (1994).

*Primary Examiner*—Porfirio Nazario-Gonzalez
*Attorney, Agent, or Firm*—Keil & Weinkauf

[57] ABSTRACT

In metal complexes of the formula I

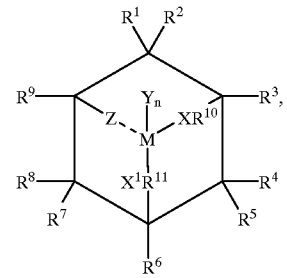

the substituents have the following meanings:

M is a metal of transition group III, IV, V or VI of the Periodic Table of the Elements or a metal of the lanthanide series, Y is a negative leaving atom or a negative leaving group, X and $X^1$ are negatively charged or uncharged atoms of main group IV, V or VI of the Periodic Table of the Elements, Z is hydrogen, $C_1$–$C_{10}$-alkyl, $C_3$–$C_{10}$-cycloalkyl, $C_1$–$C_{10}$-alkoxy, $C_1$–$C_{10}$-alkylthio or dialkylamido having from 1 to 4 carbon atoms in each alkyl radical, $R^1$ to $R^{11}$ are hydrogen, carboorganic or organosilicon radicals, n is 0, 1 or 2 and the valence of M is 2+n.

8 Claims, No Drawings

METAL COMPLEXES WITH AN ADAMANTANE-LIKE STRUCTURE

The present invention relates to metal complexes of the formula I

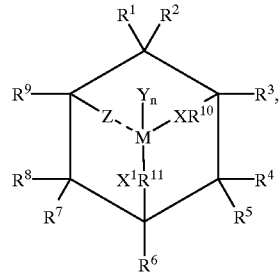

where the substituents have the following meanings:
M is a metal of transition group III, IV, V or VI of the Periodic Table of the Elements or a metal of the lanthanide series,
Y is a negative leaving atom or a negative leaving group,
X and $X^1$ are negatively charged or uncharged atoms of main group IV, V or VI of the Periodic Table of the Elements,
Z is hydrogen, $C_1$–$C_{10}$-alkyl, $C_3$–$C_{10}$-cycloalkyl, $C_1$–$C_{10}$-alkoxy, $C_1$–$C_{10}$-alkylthio or dialkylamido having from 1 to 4 carbon atoms in each alkyl radical,
$R^1$ to $R^{11}$ are hydrogen, carboorganic or organosilicon radicals, n is 0, 1 or 2 and 40 the valence of M is 2+n.

The present invention further relates to a process for preparing such metal complexes and to their use as constituents of a catalyst system for polymerizing olefinically unsaturated compounds.

Metallocene complexes are known as constituents of catalyst complexes for polymerizing olefinically unsaturated compounds. For example, WO 95/06071 describes heterofunctional compounds containing cyclopentadienyl radicals. However, this class of compounds is not able to effectively suppress chain transfer by β-hydride elimination, which leads to premature stopping of the polymerization and thereby to limited molecular weights.

DE-A 44 20 783 discloses heterofunctional, cyclopentadienyl-free compounds which, however, have an open catalyst structure and are therefore not stereoselective or favor chain transfer by β-hydrogen elimination.

It is an object of the present invention to provide novel metal complexes which can be used as constituents of catalyst systems for polymerizing olefinically unsaturated compounds and in the process effectively suppress β-hydrogen elimination and are stereoselective. In addition, the novel metal complexes should be simple to prepare.

We have found that this object is achieved by the metal complexes defined at the outset.

We have also found a process for preparing such metal complexes and also their use as constituents of a catalyst system for polymerizing olefinically unsaturated compounds.

Among the metal complexes of the formula I, preference is given to those in which the substituents have the following meanings:
M is a metal of transition group IV or V of the Periodic Table of the Elements, preferably a metal of transition group IV, i.e. titanium, zirconium or hafnium, in particular titanium,
Y is hydrogen, $C_1$–$C_{10}$-alkyl, $C_3$–$C_{10}$-cycloalkyl, $C_1$–$C_{10}$-alkoxy, dialkylamido, alkylaryl, arylalkyl, haloalkyl or haloaryl each having from 1 to carbon atoms in the alkyl radical and from 6 to 20 carbon atoms in the aryl radical, or fluorine, chlorine, bromine or iodine, preferably $C_1$–$C_4$-alkyl, $C_1$–$C_4$-alkoxy or chlorine, in particular methyl, isobutyl, methoxy, isopropoxy or chlorine,
X and $X^1$ are negatively charged atoms of main group V or VI of the Periodic Table of the Elements, preferably N, P, O or S as anion,
Z is hydrogen, $C_1$–$C_4$-alkyl or $C_4$–$C_6$-cycloalkyl, preferably hydrogen, methyl, ethyl, n-propyl or cyclohexyl,
$R^1$ to $R^{11}$ are hydrogen, $C_1$–$C_{10}$-alkyl, $C_3$–$C_{10}$-cycloalkyl, $C_6$–$C_{20}$-aryl, alkylaryl, arylalkyl, haloalkyl or haloaryl each having from 1 to 10 carbon atoms in the alkyl radical and from 6 to 20 carbon atoms in the aryl radical, or fluorine, chlorine, bromine or iodine, or two adjacent radicals may together form a cyclic group having from 4 to 5 carbon atoms, or $Si(R^{12})_3$ where
$R^{12}$ is $C_1$–$C_{10}$-alkyl, $C_3$–$C_{10}$-cycloalkyl or $C_6$–$C_{15}$-aryl, and
n is preferably 2, so that the valence of M is preferably +4.
$R^1$ to $R^{11}$ are preferably hydrogen or $C_1$–$C_{10}$-alkyl, in particular
$R^1$ to $R^8$ are hydrogen, methyl or ethyl,
$R^9$ is hydrogen, methyl, ethyl or n-propyl and
$R^{10}$ and $R^{11}$ are methyl, ethyl, n-propyl or isopropyl.

Examples of particularly preferred metal complexes of the formula I are:
5,5-dimethyl-1,3-di(methylamido)cyclohexanetitanium dichloride
5,5-diethyl-1,3-di(methylamido)cyclohexanetitanium dichloride
5,5-dipropyl-1,3-di(methylamido)cyclohexanetitanium dichloride
5,5-diisopropyl-1,3-di(methylamido)cyclohexanetitanium dichloride
5,5-dibutyl-1,3-di(methylamido)cyclohexanetitanium dichloride
5,5-di-sec-butyl-1,3-di(methylamido)cyclohexanetitanium dichloride
5,5-di-tert-butyl-1,3-di(methylamido)cyclohexanetitanium dichloride
5,5-dimethyl-1,3-di(ethylamido)cyclohexanetitanium dichloride
5,5-diethyl-1,3-di(ethylamido)cyclohexanetitanium dichloride
5,5-dipropyl-1,3-di(ethylamido)cyclohexanetitanium dichloride
5,5-diisopropyl-1,3-di(ethylamido)cyclohexanetitanium dichloride
5,5-di-sec-butyl-1,3-di(ethylamido)cyclohexanetitanium dichloride
5,5-di-tert-butyl-1,3-di(ethylamido)cyclohexanetitanium dichloride
5,5-dimethyl-1,3-di(propylamido)cyclohexanetitanium dichloride
5,5-diethyl-1,3-di(propylamido)cyclohexanetitanium dichloride
5,5-dipropyl-1,3-di(propylamido)cyclohexanetitanium dichloride
5,5-diisopropyl-1,3-di(propylamido)cyclohexanetitanium dichloride
5,5-dibutyl-1,3-di(propylamido)cyclohexanetitanium dichloride
5,5-di-sec-butyl-1,3-di(propylamido)cyclohexanetitanium dichloride
5,5-di-tert-butyl-1,3-di(propylamido)cyclohexanetitanium dichloride
5,5-dimethyl-1,3-di(propylamido)cyclohexanetitanium dichloride 5,5-diethyl-1,3-di(isopropylamido)cyclohexanetitanium dichloride
5,5-dipropyl-1,3-di(isopropylamido)cyclohexanetitanium dichloride
5,5-diisopropyl-1,3-di(isopropylamido)cyclohexanetitanium dichloride
5,5-dibutyl-1,3-di(isopropylamido)cyclohexanetitanium dichloride
5,5-di-sec-butyl-1,3-di(isopropylamido)cyclohexanetitanium dichloride
5,5-di-tert-butyl-1,3-di(isopropylamido)cyclohexanetitanium dichloride
5,5-dimethyl-1,3-di(butylamido)cyclohexanetitanium dichloride
5,5-diethyl-1,3-di(butylamido)cyclohexanetitanium dichloride
5,5-dipropyl-1,3-di(butylamido)cyclohexanetitanium dichloride
5,5-diisopropyl-1,3-di(butylamido)cyclohexanetitanium dichloride
5,5-dibutyl-1,3-di(butylamido)cyclohexanetitanium dichloride
5,5-di-sec-butyl-1,3-di(butylamido)cyclohexanetitanium dichloride
5,5-di-tert-butyl-1,3-di(butylamido)cyclohexanetitanium dichloride
5,5-dimethyl-1,3-di(methylamido)cyclohexanedimethyltitanium
5,5-diethyl-1,3-di(methylamido)cyclohexanedimethyltitanium
5,5-dipropyl-1,3-di(methylamido)cyclohexanedimethyltitanium
5,5-diisopropyl-1,3-di(methylamido)cyclohexanedimethyltitanium
5,5-dibutyl-1,3-di(methylamido)cyclohexanedimethyltitanium
5,5-di-sec-butyl-1,3-di(methylamido)cyclohexanedimethyltitanium
5,5-di-tert-butyl-1,3-di(methylamido)cyclohexanedimethyltitanium
5,5-dimethyl-1,3-di(ethylamido)cyclohexanedimethyltitanium
5,5-diethyl-1,3-di(ethylamido)cyclohexanedimethyltitanium
5,5-dipropyl-1,3-di(ethylamido)cyclohexanedimethyltitanium
5,5-diisopropyl-1,3-di(ethylamido)cyclohexanetitanium dichloride
5,5-di-sec-butyl-1,3-di(ethylamido)cyclohexanedimethyltitanium
5,5-di-tert-butyl-1,3-di(ethylamido)cyclohexanedimethyltitanium
5,5-dimethyl-1,3-di(propylamido)cyclohexanedimethyltitanium
5,5-diethyl-1,3-di(propylamido)cyclohexanedimethyltitanium
5,5-dipropyl-1,3-di(propylamido)cyclohexanedimethyltitanium
5,5-diisopropyl-1,3-di(propylamido)cyclohexanedimethyltitanium
5,5-dibutyl-1,3-di(propylamido)cyclohexanedimethyltitanium
5,5-di-sec-butyl-1,3-di(propylamido)cyclohexanedimethyltitanium
5,5-di-tert-butyl-1,3-di(propylamido)cyclohexanedimethyltitanium
5,5-dimethyl-1,3-di(propylamido)cyclohexanedimethyltitanium
5,5-diethyl-1,3-di(isopropylamido)cyclohexanedimethyltitanium
5,5-dipropyl-1,3-di(isopropylamido)cyclohexanedimethyltitanium
5,5-diisopropyl-1,3-di(isopropylamido)cyclohexanedimethyltitanium
5,5-dibutyl-1,3-di(isopropylamido)cyclohexanedimethyltitanium
5,5-di-sec-butyl-1,3-di(isopropylamido)cyclohexanedimethyltitanium
5,5-di-tert-butyl-1,3-di(isopropylamido)cyclohexanedimethyltitanium
5,5-dimethyl-1,3-di(butylamido)cyclohexanedimethyltitanium
5,5-diethyl-1,3-di(butylamido)cyclohexanedimethyltitanium
5,5-dipropyl-1,3-di(butylamido)cyclohexanedimethyltitanium
5,5-diisopropyl-1,3-di(butylamido)cyclohexanedimethyltitanium
5,5-dibutyl-1,3-di(butylamido)cyclohexanedimethyltitanium
5,5-di-sec-butyl-1,3-di(butylamido)cyclohexanedimethyltitanium
5,5-di-tert-butyl-1,3-di(butylamido)cyclohexanedimethyltitanium
5,5-dimethyl-1,3-di(methylamido)cyclohexanetitanium diisopropoxide
5,5-diethyl-1,3-di(methylamido)cyclohexanetitanium diisopropoxide
5,5-dipropyl-1,3-di(methylamido)cyclohexanetitanium diisopropoxide
5,5-diisopropyl-1,3-di(methylamido)cyclohexanetitanium diisopropoxide
5,5-dibutyl-1,3-di(methylamido)cyclohexanetitanium diisopropoxide
5,5-di-sec-butyl-1,3-di(methylamido)cyclohexanetitanium diisopropoxide
5,5-di-tert-butyl-1,3-di(methylamido)cyclohexanetitanium diisopropoxide
5,5-dimethyl-1,3-di(ethylamido)cyclohexanetitanium diisopropoxide
5,5-diethyl-1,3-di(ethylamido)cyclohexanetitanium diisopropoxide
5,5-dipropyl-1,3-di(ethylamido)cyclohexanetitanium diisopropoxide
5,5-diisopropyl-1,3-di(ethylamido)cyclohexanetitanium diisopropoxide
5,5-di-sec-butyl-1,3-di(ethylamido)cyclohexanetitanium diisopropoxide
5,5-di-tert-butyl-1,3-di(ethylamido)cyclohexanetitanium diisopropoxide
5,5-dimethyl-1,3-di(propylamido)cyclohexanetitanium diisopropoxide
5,5-diethyl-1,3-di(propylamido)cyclohexanetitanium diisopropoxide
5,5-dipropyl-1,3-di(propylamido)cyclohexanetitanium diisopropoxide
5,5-diisopropyl-1,3-di(propylamido)cyclohexanetitanium diisopropoxide
5,5-dibutyl-1,3-di(propylamido)cyclohexanetitanium diisopropoxide
5,5-di-sec-butyl-1,3-di(propylamido)cyclohexanetitanium diisopropoxide
5,5-di-tert-butyl-1,3-di(propylamido)cyclohexanetitanium diisopropoxide
5,5-dimethyl-1,3-di(propylamido)cyclohexanetitanium diisopropoxide 5,5-diethyl-1,3-di(isopropylamido)cyclohexanetitanium diisopropoxide
5,5-dipropyl-1,3-di(isopropylamido)cyclohexanetitanium diisopropoxide
5,5-diisopropyl-1,3-di(isopropylamido)cyclohexanetitanium diisopropoxide
5,5-dibutyl-1,3-di(isopropylamido)cyclohexanetitanium diisopropoxide
5,5-di-sec-butyl-1,3-di(isopropylamido)cyclohexanetitanium diisopropoxide
5,5-di-tert-butyl-1,3-di(isopropylamido)cyclohexanetitanium diisopropoxide
5,5-dimethyl-1,3-di(butylamido)cyclohexanetitanium diisopropoxide
5,5-diethyl-1,3-di(butylamido)cyclohexanetitanium diisopropoxide
5,5-dipropyl-1,3-di(butylamido)cyclohexanetitanium diisopropoxide
5,5-diisopropyl-1,3-di(butylamido)cyclohexanetitanium diisopropoxide
5,5-dibutyl-1,3-di(butylamido)cyclohexanetitanium diisopropoxide
5,5-di-sec-butyl-1,3-di(butylamido)cyclohexanetitanium diisopropoxide
5,5-di-tert-butyl-1,3-di(butylamido)cyclohexanetitanium diisopropoxide
5,5-dimethyl-1,3-di(methylphosphido)cyclohexanetitanium dichloride
5,5-diethyl-1,3-di(methylphosphido)cyclohexanetitanium dichloride
5,5-dipropyl-1,3-di(methylphosphido)cyclohexanetitanium dichloride
5,5-diisopropyl-1,3-di(methylphosphido)cyclohexanetitanium dichloride
5,5-dibutyl-1,3-di(methylphosphido)cyclohexanetitanium dichloride
5,5-di-sec-butyl-1,3-di(methylphosphido)cyclohexanetitanium dichloride
5,5-di-tert-butyl-1,3-di(methylphosphido)cyclohexanetitanium dichloride
5,5-dimethyl-1,3-di(ethylphosphido)cyclohexanetitanium dichloride
5,5-diethyl-1,3-di(ethylphosphido)cyclohexanetitanium dichloride
5,5-dipropyl-1,3-di(ethylphosphido)cyclohexanetitanium dichloride
5,5-diisopropyl-1,3-di(ethylphosphido)cyclohexanetitanium dichloride
5,5-di-sec-butyl-1,3-di(ethylphosphido)cyclohexanetitanium dichloride
5,5-di-tert-butyl-1,3-di(ethylphosphido)cyclohexanetitanium dichloride
5,5-dimethyl-1,3-di(propylphosphido)cyclohexanetitanium dichloride
5,5-diethyl-1,3-di(propylphosphido)cyclohexanetitanium dichloride
5,5-dipropyl-1,3-di(propylphosphido)cyclohexanetitanium dichloride
5,5-diisopropyl-1,3-di(propylphosphido)cyclohexanetitanium dichloride
5,5-dibutyl-1,3-di(propylphosphido)cyclohexanetitanium dichloride
5,5-di-sec-butyl-1,3-di(propylphosphido)cyclohexanetitanium dichloride
5,5-di-tert-butyl-1,3-di(propylphosphido)cyclohexanetitanium dichloride
5,5-dimethyl-1,3-di(propylphosphido)cyclohexanetitanium dichloride
5,5-diethyl-1,3-di(isopropylphosphido)cyclohexanetitanium dichloride
5,5-dipropyl-1,3-di(isopropylphosphido)cyclohexanetitanium dichloride
5,5-diisopropyl-1,3-di(isopropylphosphido)cyclohexanetitanium dichloride
5,5-dibutyl-1,3-di(isopropylphosphido)cyclohexanetitanium dichloride
5,5-di-sec-butyl-1,3-di(isopropylphosphido)cyclohexanetitanium dichloride
5,5-di-tert-butyl-1,3-di(isopropylphosphido)cyclohexanetitanium dichloride
5,5-dimethyl-1,3-di(butylphosphido)cyclohexanetitanium dichloride
5,5-diethyl-1,3-di(butylphosphido)cyclohexanetitanium dichloride
5,5-dipropyl-1,3-di(butylphosphido)cyclohexanetitanium dichloride
5,5-diisopropyl-1,3-di(butylphosphido)cyclohexanetitanium dichloride
5,5-dibutyl-1,3-di(butylphosphido)cyclohexanetitanium dichloride
5,5-di-sec-butyl-1,3-di(butylphosphido)cyclohexanetitanium dichloride
5,5-di-tert-butyl-1,3-di(butylphosphido)cyclohexanetitanium dichloride
5,5-dimethyl-1,3-di(methylphosphido)cyclohexanedimethyltitanium
5,5-diethyl-1,3-di(methylphosphido)cyclohexanedimethyltitanium
5,5-dipropyl-1,3-di(methylphosphido)cyclohexanedimethyltitanium
5,5-diisopropyl-1,3-di(methylphosphido)cyclohexanedimethyltitanium titanium
5,5-dibutyl-1,3-di(methylphosphido)cyclohexanedimethyltitanium
5,5-di-sec-butyl-1,3-di(methylphosphido)cyclohexanedimethyltitanium
5,5-di-tert-butyl-1,3-di(methylphosphido)cyclohexanedimethyltitanium
5,5-dimethyl-1,3-di(ethylphosphido)cyclohexanedimethyltitanium
5,5-diethyl-1,3-di(ethylphosphido)cyclohexanedimethyltitanium
5,5-dipropyl-1,3-di(ethylphosphido)cyclohexanedimethyltitanium
5,5-diisopropyl-1,3-di(ethylphosphido)cyclohexanetitanium dichloride
5,5-di-sec-butyl-1,3-di(ethylphosphido)cyclohexanedimethyltitanium
5,5-di-tert-butyl-1,3-di(ethylphosphido)cyclohexanedimethyltitanium
5,5-dimethyl-1,3-di(propylphosphido)cyclohexanedimethyltitanium
5,5-diethyl-1,3-di(propylphosphido)cyclohexanedimethyltitanium
5,5-dipropyl-1,3-di(propylphosphido)cyclohexanedimethyltitanium
5,5-diisopropyl-1,3-di(propylphosphido)cyclohexanedimethyltitanium
5,5-dibutyl-1,3-di(propylphosphido)cyclohexanedimethyltitanium
5,5-di-sec-butyl-1,3-di(propylphosphido)cyclohexanedimethyltitanium
5,5-di-tert-butyl-1,3-di(propylphosphido)cyclohexanedimethyltitanium
5,5-dimethyl-1,3-di(propyphosphido)cyclohexanedimethyltitanium 5,5-diethyl-1,3-di(isopropylphosphido)
   cyclohexanedimethyltitanium
5,5-dipropyl-1,3-di(isopropylphosphido)
   cyclohexanedimethyltitanium
5,5-diisopropyl-1,3-di(isopropylphosphido)
   cyclohexanedimethyltitanium
5,5-dibutyl-1,3-di(isopropylphosphido)
   cyclohexanedimethyltitanium
5,5-di-sec-butyl-1,3-di(isopropylphosphido)
   cyclohexanedimethyltitanium
5,5-di-tert-butyl-1,3-di(isopropylphosphido)
   cyclohexanedimethyltitanium
5,5-dimethyl-1,3-di(butylphosphido)
   cyclohexanedimethyltitanium
5,5-diethyl-1,3-di(butylphosphido)
   cyclohexanedimethyltitanium
5,5-dipropyl-1,3-di(butylphosphido)
   cyclohexanedimethyltitanium
5,5-diisopropyl-1,3-di(butylphosphido)
   cyclohexanedimethyltitanium
5,5-dibutyl-1,3-di(butylphosphido)
   cyclohexanedimethyltitanium
5,5-di-sec-butyl-1,3-di(butylphosphido)
   cyclohexanedimethyltitanium
5,5-di-tert-butyl-1,3-di(butylphosphido)
   cyclohexanedimethyltitanium
5,5-dimethyl-1,3-di(methylphosphido)cyclohexanetitanium
   diisopropoxide
5,5-diethyl-1,3-di(methylphosphido)cyclohexanetitanium
   diisopropoxide
5,5-dipropyl-1,3-di(methylphosphido)cyclohexanetitanium
   diisopropoxide
5,5-diisopropyl-1,3-di(methylphosphido)
   cyclohexanetitanium diisopropoxide
5,5-dibutyl-1,3-di(methylphosphido)cyclohexanetitanium
   diisopropoxide
5,5-di-sec-butyl-1,3-di(methylphosphido)
   cyclohexanetitanium diisopropoxide
5,5-di-tert-butyl-1,3-di(methylphosphido)
   cyclohexanetitanium diisopropoxide
5,5-dimethyl-1,3-di(ethylphosphido)cyclohexanetitanium
   diisopropoxide
5,5-diethyl-1,3-di(ethylphosphido)cyclohexanetitanium
   diisopropoxide
5,5-dipropyl-1,3-di(ethylphosphido)cyclohexanetitanium
   diisopropoxide
5,5-diisopropyl-1,3-di(ethylphosphido)cyclohexanetitanium
   diisopropoxide
5,5-di-sec-butyl-1,3-di(ethylphosphido)
   cyclohexanetitanium diisopropoxide
5,5-di-tert-butyl-1,3-di(ethylphosphido)
   cyclohexanetitanium diisopropoxide
5,5-dimethyl-1,3-di(propylphosphido)cyclohexanetitanium
   diisopropoxide
5,5-diethyl-1,3-di(propylphosphido)cyclohexanetitanium
   diisopropoxide
5,5-dipropyl-1,3-di(propylphosphido)cyclohexanetitanium
   diisopropoxide
5,5-diisopropyl-1,3-di(propylphosphido)
   cyclohexanetitanium diisopropoxide
5,5-dibutyl-1,3-di(propylphosphido)cyclohexanetitanium
   diisopropoxide
5,5-di-sec-butyl-1,3-di(propylphosphido)
   cyclohexanetitanium diisopropoxide
5,5-di-tert-butyl-1,3-di(propylphosphido)
   cyclohexanetitanium diisopropoxide
5,5-dimethyl-1,3-di(propylphosphido)cyclohexanetitanium
   diisopropoxide
5,5-diethyl-1,3-di(isopropylphosphido)cyclohexanetitanium
   diisopropoxide
5,5-dipropyl-1,3-di(isopropylphosphido)
   cyclohexanetitanium diisopropoxide
5,5-diisopropyl-1,3-di(isopropylphosphido)
   cyclohexanetitanium diisopropoxide
5,5-dibutyl-1,3-di(isopropylphosphido)
   cyclohexanetitanium diisopropoxide
5,5-di-sec-butyl-1,3-di(isopropylphosphido)
   cyclohexanetitanium diisopropoxide
5,5-di-tert-butyl-1,3-di(isopropylphosphido)
   cyclohexanetitanium diisopropoxide
5,5-dimethyl-1,3-di(butylphosphido)cyclohexanetitanium
   diisopropoxide
5,5-diethyl-1,3-di(butylphosphido)cyclohexanetitanium
   diisopropoxide
5,5-dipropyl-1,3-di(butylphosphido)cyclohexanetitanium
   diisopropoxide
5,5-diisopropyl-1,3-di(butylphosphido)
   cyclohexanetitanium diisopropoxide
5,5-dibutyl-1,3-di(butylphosphido)cyclohexanetitanium
   diisopropoxide
5,5-di-sec-butyl-1,3-di(butylphosphido)
   cyclohexanetitanium diisopropoxide
5,5-di-tert-butyl-1,3-di(butylphosphido)
   cyclohexanetitanium diisopropoxide
2,5,5-trimethyl-1,3-di(methylamido)cyclohexanetitanium
   dichloride
2,5,5-trimethyl-1,3-di(ethylamido)cyclohexanetitanium
   dichloride
2,5,5-trimethyl-1,3-di(propylamido)cyclohexanetitanium
   dichloride
2,5,5-trimethyl-1,3-di(isopropylamido)cyclohexanetitanium
   dichloride
2,5,5-trimethyl-1,3-di(butylamido)cyclohexanetitanium
   dichloride
2,5,5-trimethyl-1,3-di(methylamido)
   cyclohexanedimethyltitanium
2,5,5-trimethyl-1,3-di(benzylamido)cyclohexanetitanium
   dichloride
2,5,5-trimethyl-1,3-di(methylamido)cyclohexanetitanium
   dibenzyl
2-ethyl-5,5-dimethyl-1,3-di(methylamido)
   cyclohexanetitanium dichloride
2-ethyl-5,5-dimethyl-1,3-di(ethylamido)
   cyclohexanetitanium dichloride
2-ethyl-5,5-dimethyl-1,3-di(isopropylamido)
   cyclohexanetitanium dichloride
2-ethyl-5,5-dimethyl-1,3-di(propylamido)
   cyclohexanetitanium dichloride
2-ethyl-5,5-dimethyl-1,3-di(butylamido)
   cyclohexanetitanium dichloride
2-ethyl-5,5-dimethyl-1,3-di(methylamido)
   cyclohexanedimethyltitanium
2-ethyl-5,5-dimethyl-1,3-di(methylamido)
   cyclohexanedibenzyltitanium
2-butyl-5,5-dimethyl-1,3-di(methylamido)
   cyclohexanetitanium dichloride
2-butyl-5,5-dimethyl-1,3-di(ethylamido)
   cyclohexanetitanium dichloride
2-butyl-5,5-dimethyl-1,3-di(propylamido)
   cyclohexanetitanium dichloride
2-butyl-5,5-dimethyl-1,3-di(butylamido)
   cyclohexanetitanium dichloride
2-butyl-5,5-dimethyl-1,3-di(isopropylamido)
   cyclohexanetitanium dichloride
2-butyl-5,5-dimethyl-1,3-di(methylamido)
   cyclohexanedimethyltitanium 2-butyl-5,5-dimethyl-1,3-di(benzylamido)
  cyclohexanetitanium dichloride
2-butyl-5,5-dimethyl-1,3-di(methylamido)
  cyclohexanedibenzyltitanium
2-butyl-5,5-dimethyl-1,3-di(methylamido)
  cyclohexanedibutyltitanium
2-benzyl-5,5-dimethyl-1,3-di(methylamido)
  cyclohexanetitanium dichloride
2-benzyl-5,5-dimethyl-1,3-di(ethylamido)
  cyclohexanetitanium dichloride
2-benzyl-5,5-dimethyl-1,3-di(propylamido)
  cyclohexanetitanium dichloride
2-benzyl-5,5-dimethyl-1,3-di(isopropylamido)
  cyclohexanetitanium dichloride
2-benzyl-5,5-dimethyl-1,3-di(butylamido)
  cyclohexanetitanium dichloride
2-benzyl-5,5-dimethyl-1,3-di(benzylamido)
  cyclohexanetitanium dichloride
2-benzyl-5,5-dimethyl-1,3-di(methylamido)
  cyclohexanedimethyltitanium
2-benzyl-5,5-dimethyl-1,3-di(methylamido)
  cyclohexanedibutyltitanium
2-benzyl-5,5-dimethyl-1,3-di(methylamido)
  cyclohexanedibenzyltitanium
2-benzyl-5,5-dimethyl-1,3-di(benzylamido)
  cyclohexanedimethyltitanium
2-benzyl-5,5-dimethyl-1,3-di(benzylamido)
  cyclohexanedibenzyltitanium
2-benzyl-5,5-dimethyl-1,3-di(benzylamido)
  cyclohexanedibutyltitanium
2-benzyl-5,5-dimethyl-1,3-di(isopropylamido)
  cyclohexanedimethyltitanium.

The metal complexes 1,3-dimethylamido-5,5-dimethylcyclohexanetitanium dichloride, 1,3-dimethylamido-5,5-dimethylcyclohexanedimethyltitanium and 1,3-di(isopropylamido)-2,5,5-trimethylcyclohexanetitanium dichloride are particularly preferred.

The novel metal complexes of the formula I can be prepared by the following methods:

A compound of the formula II

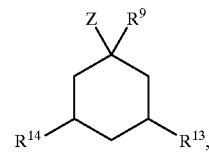

is metallated.

This is preferably done by reacting a compound of the formula II with hydrides, carboorganic compounds, nitrogenorganic compounds or organosilicon compounds of alkali metals or alkaline earth metals and then treating the product with halogen, alkoxy or aryloxy compounds of M.

Compounds of the formula II can be prepared as follows:

A compound of the formula V

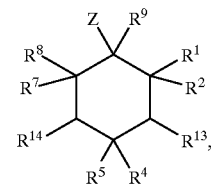

where $R^{13}$ and $R^{14}$ are $=O$, $=S$ or $=NR^{15}$ where $R^{15}$ is hydrogen, $C_1$–$C_{10}$-alkyl or $C_4$–$C_6$-cycloalkyl, can be reacted with hydrides or amides of alkali metals or alkaline earth metals or with carboorganic compounds or organosilicon compounds, which may also contain halogens, to give compounds of the formula IV

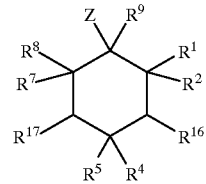

which may be reduced to give compounds of the formula III

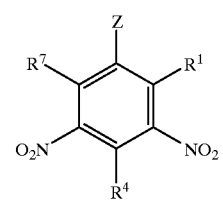

where $R^{16}$ and $R^{17}$ are —OH, —SH, —NHR$^{15}$, and these can be converted into compounds of the formula II by introducing, if desired, tosylate, mesylate or triflate groups and subsequently treating with amine, alkali metal amide or alkali metal phosphide.

Compounds of the formula II can also be prepared as follows:

A compound of the formula VI

VI is reduced to give compounds of the formula VII

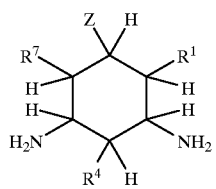

VII which can be alkylated on the nitrogen to give compounds of the formula II.

The preparation of compounds of the formula I is preferably carried out by dissolving a compound of the formula II in a solvent such as THF, diethyl ether, dioxane or toluene, preferably in THF, and reacting it at from −78 to 60° C. with preferably a 2.1 molar amount of metallating reagents such as alkali metal hydrides, butyllithium, methyllithium, phenyllithium, naphthalenesodium, lithium diisopropylamide or lithium bis(trimethylsilyl)amide, preferably butyllithium, and subsequently reacting the product with transition metal halides, alkoxides or amides, preferably chlorides, or transition metal chloride-THF complexes.

If desired, compounds of the formula I can be modified by replacement of the halogen ligands on M. Preferably, compounds of the formula I are dissolved in solvents such as THF, diethyl ether or toluene at from −78 to 100° C. and treated with an at least twice molar amount of methylmagnesium chloride, butyllithium, methyllithium or benzylmagnesium bromide to give alkyl or arylalkyl derivatives of compounds of the formula I.

The compounds of the formula II are preferably obtained by
A) if appropriate, reaction of compounds of the formula V with alkali metal hydrides, butyllithium, methyllithium, phenyllithium, naphthalenesodium, lithium diisopropylamide, lithium bis(trimethylsilyl)amide or alkali metal alkoxides, preferably lithium diisopropylamide or potassium tert-butoxide, in solvents such as THF, diethyl ether, dioxane, toluene or alcohols, preferably THF or butanol, at from −78 to 65° C. with a 1–3.5 molar amount of alkyl halides, trialkylsilyl chlorides or arylalkyl halides to give compounds of the formula IV. Compounds of the formula IV are preferably reduced to compounds of the formula III by reaction with lithium aluminum hydride, sodium borohydride or other customary reducing agents, where a twice molar amount of reducing agent is added at from −78 to 100° C. in THF, diethyl ether, dioxane or toluene. Compounds of the formula III are preferably reacted with p-toluenesulfonyl chloride, trifluoromethanesulfonic anhydride or methanesulfonyl chloride, particularly preferably trifluoromethanesulfonic anhydride, in the presence of 1–2 molar amounts of bases such as pyridine, quinoline or triethylamine in solvents such as THF, DMF, acetonitrile, dimethyl sulfoxide, diethyl ether or methylene chloride at from −78 to 60° C. The intermediates are preferably reacted in situ with methylamine, lithium isopropylamide, lithium methylamide, lithium butylphosphide or lithium phenylphosphide at from −78 to 60° C. to give compounds of the formula II.
B) Compounds of the formula VII are preferably obtained by reducing compounds of the formula VI with hydrogen, if desired in the presence of catalysts such as Ni, platinum, Raney nickel or ruthenium, in solvents such as THF, toluene, diethyl ether, dioxane or methanol at from −78 to 120° C.

Compounds of the formula VII can, if appropriate, be dissolved in solvents such as THF, diethyl ether or toluene and reacted at from −78 to 80° C. with customary alkylating agents, for example methyl iodide or isopropyl bromide, to give compounds of the formula II.

The metal complexes of the present invention are simple to prepare and are suitable as constituents of catalyst systems for polymerizing olefinically unsaturated compounds. The adamantane-like structure of the metal complexes of the present invention is achieved by reversible agostic coordination, giving a stereoselective catalyst system which effectively suppresses chain transfer by β-hydride elimination.

EXAMPLES

Example 1

Preparation of 1,3-dimethylamido-5,5-dimethylcyclohexanetitanium dichloride I1 a) 5,5-dimethylcyclohexane-1,3-diol 14.0 g (0.1 mol) of dimedone were dissolved in 200 ml of THF. 3.8 g (0.1 mol) of $NaBH_4$ and 5 mmol of $CeCl_3$ dissolved in 50 ml of THF were then added at −30° C. The mixture was stirred at room temperature for another 2 hours and was hydrolyzed at 0° C. by means of methanol/water. The organic phase was separated off and the solvent was removed. The residue was extracted with ethanol and unreacted dimedone was removed by crystallization. This gave 11.5 g (80%) of 5,5-dimethylcyclohexane-1,3-diol.

b) 5,5-dimethylcyclohexane 1,3-ditosylate 0.28 mol of absolute pyridine was carefully added at 0° C. to a solution of 10.8 g (75 mmol) of 5,5-dimethylcyclohexane-1,3-diol and 26.7 g (0.14 mol) of p-toluenesulfonyl chloride in 180 ml of methylene chloride. After warming to room temperature, the mixture was stirred for a further 2 hours and subsequently hydrolyzed by addition of 100 g of ice and 30 ml of concentrated sulfuric acid. The organic phase was separated off and the solvent was removed under reduced pressure. The crude product was recrystallized from methylene chloride/diethyl ether. Yield: 22.2 g (70%).

c) 1,3-dimethylamino-5,5-dimethylcyclohexane 20.3 g (45 mmol) of 5,5-dimethylcyclohexane 1,3-ditosylate were dissolved in 200 ml of ethanol/water and admixed with 90 mmol of aqueous methylamine. The mixture was stirred for 12 hours at room temperature. After addition of sodium bicarbonate, the solution was extracted a number of times with diethyl ether. The ether extracts were evaporated to dryness and the crude product was washed with water. Yield: 6.1 g (79%).

d) 1,3-dimethylamido-5,5-dimethylcyclohexanetitanium dichloride I1

5.1 g (30 mmol) of 1,3-dimethylamino-5,5-dimethylcyclohexane were dissolved in 75 ml of THF at −78° C. and admixed with 60 mmol of n-butyllithium. The mixture was warmed to room temperature and stirred for 12 hours. The solvent was removed and the residue was digested a number of times with diethyl ether. The resulting 1,3-dimethylamido-5,5-dimethylcyclohexanedilithium compound was redissolved at −78° C. in 75 ml of absolute THF and admixed with a solution of 5.9 g (31 mmol) of $TiCl_4$ in 15 ml of THF. The cooling was removed and the mixture was stirred for a further 15 hours. The precipitated LiCl was filtered off and the THF solution was evaporated under reduced pressure. The oil which remained was recrystallized from diethyl ether/THF, giving a crystalline solid. Yield: 6.7 g (78%).

Example 2
Preparation of 1,3-dimethylamido-5,5-dimethylcyclohexanedimethyltitanium I2

At −78° C., 33.3 ml (0.1 mol) of a 3.0 M solution of methylmagnesium chloride in THF were added to 14.3 g (0.05 mol) of 1,3-dimethylamido-5,5-dimethylcyclohexanetitanium dichloride I1. The cooling was removed and the mixture was warmed to room temperature over a period of 4 hours. The solvent was removed under reduced pressure and the oily suspension which remained was extracted with diethyl ether. The combined ether extracts were evaporated and the product was crystallized by cooling to −30° C. This gave 6.9 g (56%) of pale yellow crystals.

Example 3
Preparation of 1,3-di(isopropylamido)-2,5,5-trimethylcyclohexanetitanium dichloride I3 a) 2,5,5-trimethylcyclohexane-1,3-dione 28.0 g (0.2 mol) of dimedone were dissolved in 150 ml of absolute t-butanol and, at 40° C., 22.4 g (0.2 mol) of potassium t-butoxide were added a little at a time. After 2 hours, an equimolar amount of methyl iodide was added. After a further 2 hours, the solvent was removed under reduced pressure and the residue which remained was extracted 3 times with diethyl ether. The combined ether extracts were evaporated to dryness. Yield: 26.2 g (85%). The crude product was not purified further.

b) 2,5,5-trimethylcyclohexane-1,3-diol 23.1 g (0.15 mol) of 2,5,5-trimethylcyclohexane-1,3-dione were dissolved in 200 ml of THF at −30° C. and 5.7 g (0.15 mol) of $LiAlH_4$ were added carefully. The mixture was stirred for minutes at −30° C. and subsequently for 15 hours at room temperature. The unreacted $LiAlH_4$ was deactivated by addition of 50 ml of absolute methanol. The reaction mixture was extracted a number of times with dichloromethane and the organic phase was separated off and evaporated. The diol was obtained as a cis/trans mixture in a yield of 90% (21.3 g).

c) 2,5,5-trimethylcyclohexane 1,3-ditosylate 0.38 mol of absolute pyridine was carefully added at 0° C. to a solution of 15.8 g (0.1 mol) of 2,5,5-trimethylcyclohexane-1,3-diol and 36.2 g (0.19 mol) of p-toluenesulfonyl chloride in 200 ml of methylene chloride. After warming to room temperature, the mixture was stirred for another 2 hours and was subsequently hydrolyzed by addition of 160 g of ice and 45 ml of concentrated sulfuric acid. The organic phase was separated off and the solvent was removed under reduced pressure. The crude product was recrystallized from methylene chloride/diethyl ether. Yield: 31.0 g (70%).

d) 1,3-di(isopropylamino)-2,5,5-trimethylcyclohexane 30.3 g (0.065 mol) of 2,5,5-trimethylcyclohexane 1,3-ditosylate were dissolved in 250 ml of THF at −30° C. and admixed with 0.13 mol of lithium isopropylamide. The mixture was stirred at this temperature for 2 hours and subsequently left for a further 12 hours at room temperature. The THF was removed under reduced pressure and the residue was extracted with diethyl ether. The ether was removed and the crude product was used further. Yield: 14.8 g (95%).

e) 1,3-di(isopropylamido)-2,5,5-trimethylcyclohexanetitanium dichloride I3

The crude 1,3-di(isopropylamino)-2,5,5-trimethylcyclohexane (14.8 g; 0.062 mol) was dissolved in 100 ml of THF at −78° C. and admixed with 0.124 mol of n-butyllithium. After 30 minutes, the cooling was removed and the mixture was stirred for a further 2 hours at room temperature. The solution was evaporated to dryness and the residue was digested a number of times at −78° C. with diethyl ether/hexane. The colorless product which remained was redissolved in 100 ml of THF and cooled to −78° C. 12.3 g (65 mmol) of $TiCl_4$ were added over a period of 30 minutes and the mixture was stirred for a further 12 hours at room temperature. The THF was removed and the residue was extracted a number of times with diethyl ether. The combined ether extracts were evaporated and the crude product was recrystallized from diethyl ether/THF. Yield: 14.4 g (65%).

Comparative Example C1
Preparation of (N,N'-dimethylamido-1,2-ethane)titanium dichloride 3.5 g (40 mmol) of N,N'-dimethylethylenediamine were dissolved in 60 ml of THF at −78° C. and admixed with 80 mmol of n-butyllithium. The mixture was warmed to room temperature and stirred for 12 hours. The solvent was removed and the residue was again digested with a 1:1 mixture of diethyl ether and n-hexane.

The resulting (N,N'-dimethylamido-1,2-ethane)dilithium compound was dissolved in 75 ml of absolute THF at −78° C. and admixed with 8.0 g (42 mmol) of titanium tetrachloride. The cooling was removed and the mixture was stirred for a further 12 hours. The precipitated LiCl was filtered off and the THF solution was evaporated under reduced pressure. The oil which remained was recrystallized from diethyl ether, giving a crystalline solid. Yield: 5.9 g (72%).

We claim:

1. A metal complex of the formula I

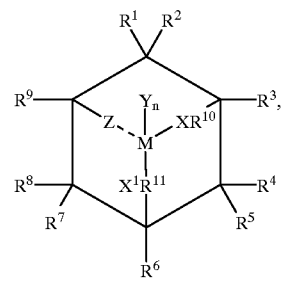

where the substituents have the following meanings:

M is a metal of transition group III, IV, V or VI of the Periodic Table of the Elements or a metal of the lanthanide series, Y is a negative leaving atom or a negative leaving group, X and $X^1$ are negatively charged or uncharged atoms of main group V or VI of the Periodic Table of the Elements, Z is hydrogen, $C_1$–$C_{10}$-alkyl, $C_3$–$C_{10}$-cycloalkyl, $C_1$–$C_{10}$-alkoxy, $C_1$–$C_{10}$-alkylthio or dialkylamido having from 1 to 4 carbon atoms in each alkyl radical, $R^1$ to $R^{11}$ are hydrogen, carboorganic or organosilicon radicals, n is 0, 1 or 2 and the valence of M is 2+n.

2. A metal complex as defined in claim 1, wherein M in the formula I is a metal of transition group IV or V of the Periodic Table of the Elements.

3. A metal complex as defined in claim 1, wherein Y in the formula I is hydrogen, $C_1$–$C_{10}$-alkyl, $C_3$–$C_{10}$-cycloalkyl, $C_1$–$C_{10}$-alkoxy, dialkylamido, alkylaryl, arylalkyl, haloalkyl or haloaryl each having from 1 to 10 carbon atoms in the alkyl radical and from 6 to 20 carbon atoms in the aryl radical, or fluorine, chlorine, bromine or iodine.

4. A metal complex as defined in claim 1, wherein X and $X^1$ in the formula I are each a negatively charged atom of main group VI of the Periodic Table of the Elements.

5. A metal complex as defined in claim 1, wherein X and $X^1$ in the formula I are each a negatively charged atom of main group V of the Periodic Table of the Elements.

6. A metal complex as defined in claim 1, wherein Z in the formula I is hydrogen or $C_1$–$C_4$-alkyl or $C_3$–$C_6$-cycloalkyl.

7. A metal complex as defined in claim 1, wherein $R^1$ to $R^{11}$ in the formula I are hydrogen, $C_1$–$C_{10}$-alkyl, $C_3$–$C_{10}$-cycloalkyl, $C_6$–$C_{20}$-aryl, alkylaryl, arylalkyl, haloalkyl or haloaryl each having from 1 to 10 carbon atoms in the alkyl radical and from 6 to 20 carbon atoms in the aryl radical, or fluorine, chlorine, bromine or iodine, or two adjacent radicals may together form a cyclic group having from 4 to 15 carbon atoms, or $Si(R^{12})_3$ where $R^{12}$ is $C_1$–$C_{10}$-alkyl, $C_3$–$C_{10}$-cycloalkyl or $C_6$–$C_{15}$-aryl.

8. A process for preparing a metal complex of the formula I as claimed in claim 1, which comprises metallating a compound of the formula II

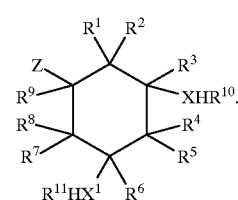

* * * * *